(12) United States Patent
Choi et al.

(10) Patent No.: US 9,816,858 B2
(45) Date of Patent: Nov. 14, 2017

(54) SENSING SYSTEM USING POSITIVE FEEDBACK INCLUDING AN AMPLIFIER AND A VOLTAGE CLAMPING DEVICE

(71) Applicant: GIPARANG CO., LTD., Seoul (KR)

(72) Inventors: Seong Wook Choi, Seoul (KR); Young June Park, Seoul (KR); Young Jun Hwang, Seoul (KR)

(73) Assignee: GIPARANG CO., LTD., Seoul (KR)

( * ) Notice: Subject to any disclaimer, the term of this patent is extended or adjusted under 35 U.S.C. 154(b) by 125 days.

(21) Appl. No.: 15/065,059

(22) Filed: Mar. 9, 2016

(65) Prior Publication Data

US 2016/0273962 A1    Sep. 22, 2016

(30) Foreign Application Priority Data

Mar. 18, 2015 (KR) ........................ 10-2015-0037281

(51) Int. Cl.
| | |
|---|---|
| *G01J 1/44* | (2006.01) |
| *G01N 21/33* | (2006.01) |
| *G01N 21/49* | (2006.01) |
| *G01N 21/63* | (2006.01) |
| *G01N 33/18* | (2006.01) |

(52) U.S. Cl.
CPC ................ *G01J 1/44* (2013.01); *G01N 21/33* (2013.01); *G01N 21/49* (2013.01); *G01N 21/63* (2013.01); *G01J 2001/446* (2013.01); *G01N 33/18* (2013.01); *G01N 2201/12* (2013.01)

(58) Field of Classification Search
CPC ........... G01J 1/44; G01N 21/49; G01N 21/63; G01N 15/06; G01N 21/27; G01N 21/5907

USPC .................................. 250/573, 214 R, 559.4
See application file for complete search history.

(56) References Cited

U.S. PATENT DOCUMENTS 5,149,983 A * 9/1992 Kaiblinger ............. B01D 53/56
250/575

FOREIGN PATENT DOCUMENTS

| JP | 7-92075 A | 4/1995 |
|---|---|---|
| JP | 7-140071 A | 6/1995 |

OTHER PUBLICATIONS

Feb. 18, 2016, Korean Office Action for related KR application No. 10-2015-0037281.

* cited by examiner

*Primary Examiner* — Que T Le
(74) *Attorney, Agent, or Firm* — Paratus Law Group, PLLC (57) ABSTRACT

Disclosed is a sensing system including an actuator configured to provide a stimulus to a detection-target material, a photo-detector configured to output an electrical signal having a snapback (SB) form corresponding to an optical reaction brought about according to the concentration of the detection-target material to which the stimulus has been provided, an amplifier configured to amplify the electrical signal output from the photo-detector and positively feedback and apply the amplified electrical signal to the actuator, a detector configured to receive the electrical signal and detect the detection-target material, and a voltage clamping device connected in parallel with the photo-detector and configured to clamp a voltage at both ends of the photo-detector so that the voltage does not exceed a predetermined voltage value.

11 Claims, 8 Drawing Sheets

SENSING SYSTEM USING POSITIVE FEEDBACK INCLUDING AN AMPLIFIER AND A VOLTAGE CLAMPING DEVICE

CROSS-REFERENCE TO RELATED APPLICATION

This application claims priority to Korean Patent Application No. 10-2015-0037281, filed on Mar. 18, 2015, the disclosure of which is incorporated herein by reference in its entirety.

BACKGROUND

1. Field of the Invention

The present invention relates to a sensing system using positive feedback.

2. Discussion of Related Art

In an existing water quality sensing system employing an actuator and a sensor, the magnitude of an input signal generated by the actuator is kept constant, and the sensor detects a change of a medium caused by the actuator. In a sensing system according to related art, the sensing system is configured to use a single ended signal scheme and/or use negative feedback scheme for a stable configuration.

As an example, in the case of a turbidity sensor, when the actuator radiates predetermined light to a medium including a material whose concentration will be measured, the sensor senses light passed through the medium and converts the light into an electrical signal, thereby measuring the concentration of the material included in the medium.

An existing sensing system has a limit of detection (LOD). For example, when the sensing system is used as a water quality sensor, even if a very small amount of material to be detected is included, that is, the amount of included material is less than the LOD, it is determined that the material is not included because the LOD characteristic of the sensing system is poor.

The present applicant applied for a patent for a sensing system which has an improved LOD to solve the aforementioned problem of the related art using positive feedback. However, according to the patent application, a photo-detector device which operates in a reverse bias state is used, and a voltage equal to or higher than a reverse breakdown voltage should be applied. In other words, the photo-detector device operates while the voltage equal to or higher than the reverse breakdown voltage is applied, and thus the device may be destroyed by the reverse breakdown voltage, that is, the problem of reliability may arise.

In addition, according to the patent application, it is possible to measure a concentration of a medium, etc. by measuring an equivalent resistance resulting from a current provided by the photo-detector and a both-end voltage, but the equivalent resistance may have a negative resistance value of giga-ohms or higher. Therefore, an expensive high-precision measuring instrument capable of measuring a resistance value of giga-ohms or higher is required.

SUMMARY OF THE INVENTION

The present invention is directed to providing a sensing system which has an improved limit of detection (LOD) characteristic to detect a very small amount of material with higher sensitivity, and supplies a sufficient current while operating at a lower voltage.

The present invention is also directed to providing a sensing system having a low resistance value which is not required to be measured using expensive equipment.

According to an aspect of the present invention, there is provided a sensing system including: an actuator configured to provide a stimulus to a detection-target material, a photo-detector configured to output an electrical signal having a snapback (SB) form corresponding to an optical reaction brought about according to a concentration of the detection-target material to which the stimulus has been provided, an amplifier configured to amplify the electrical signal output from the photo-detector and positively feedback and apply the amplified electrical signal to the actuator, a detector configured to receive the electrical signal and detect the detection-target material, and a voltage clamping device connected in parallel with the photo-detector and configured to clamp a voltage at both ends of the photo-detector so that the voltage does not exceed a predetermined voltage value.

According to another aspect of the present invention, there is provided a sensing system including: an actuator configured to provide a stimulus to a detection-target material, a photo-detector configured to output an electrical signal having an SB form corresponding to an optical reaction brought about according to a concentration of the detection-target material to which the stimulus has been provided, an amplifier configured to amplify the electrical signal output from the photo-detector and positively feedback and apply the amplified electrical signal to the actuator, a detector configured to receive the electrical signal and detect the detection-target material, and a resistance connected in parallel with the photo-detector. A resistance value of the resistance is determined so that an equivalent resistance for the photo-detector and the resistance connected in parallel has a smaller resistance value than an equivalent resistance for the photo-detector.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Specific structural and functional details disclosed herein are merely representative for purposes of describing the exemplary embodiments of the present invention, and the present invention should not be construed as limited to the exemplary embodiments. In other words, since the present invention may have various modifications and alternative forms, it should be understood that the scope of the present invention covers all modifications, equivalents, and alternatives capable of implementing the technical spirit of the present invention.

The terminology used in this specification should be understood as follows.

The singular forms "a," "an," and "the" are also intended to include the plural forms unless clearly indicates otherwise by context. It should be further understood that the terms "comprises," "comprising," "includes," and/or "including," when used herein, specify the presence of stated features, integers, steps, operations, elements, components, and/or groups thereof, but do not preclude the presence or addition of one or more other features, integers, steps, operations, elements, components, and/or groups thereof.

In reference drawings for describing exemplary embodiments of the present disclosure, size, height, thickness, etc. are intentionally exaggerated for convenience of description and ease of understanding, but are not enlarged or reduced according to a ratio. Also, in the drawings, some elements may be intentionally reduced, and other elements may be intentionally enlarged.

Unless otherwise defined, all terms used herein have the same meaning as commonly understood by those of ordinary skill in the art to which this invention pertains. It should be further understood that terms, such as those defined in commonly used dictionaries, should be interpreted as having a meaning that is consistent with their meaning in the context of the relevant art and should not be interpreted in an idealized or overly formal sense unless expressly so defined herein.

Figure 1:
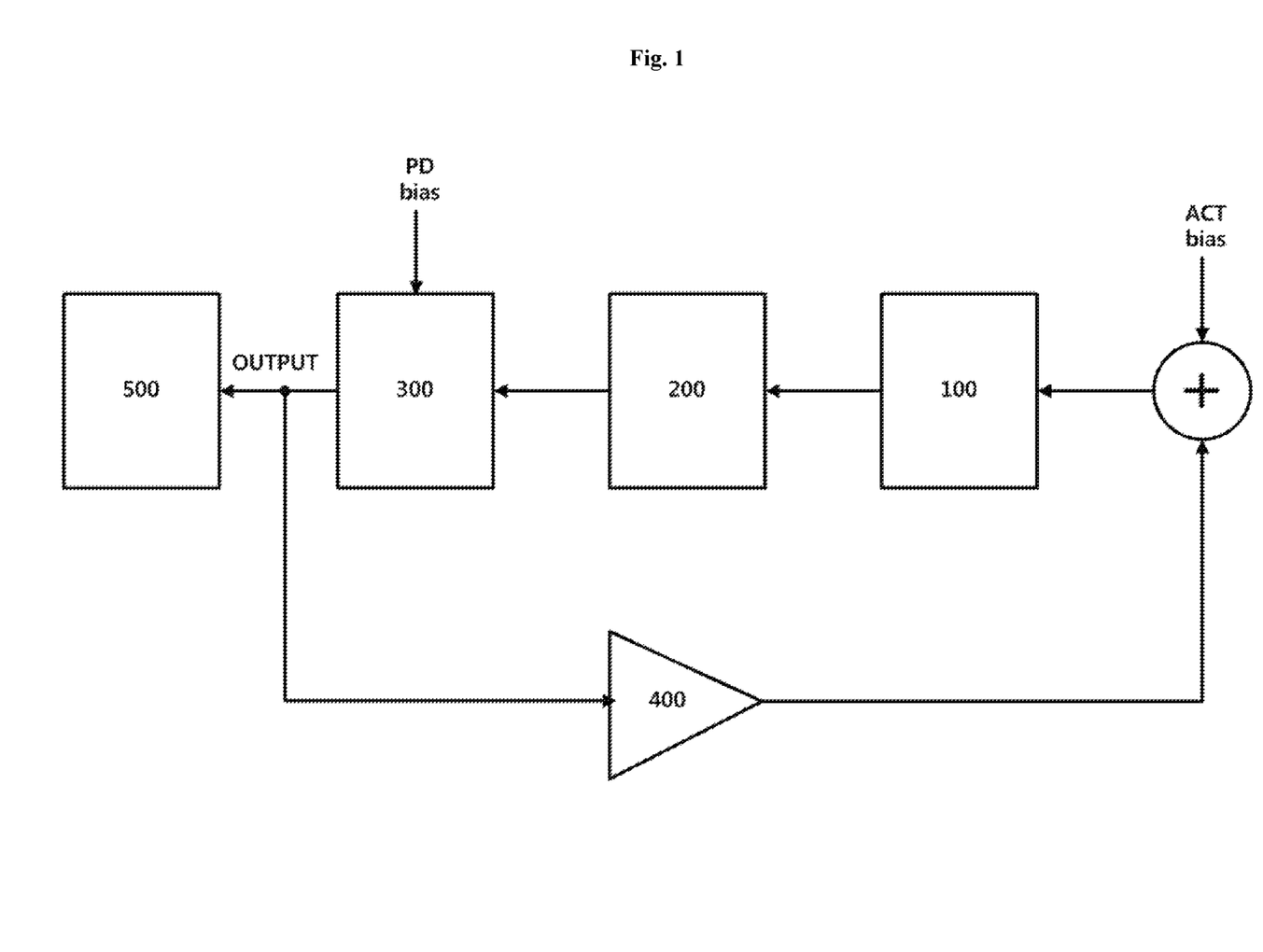
FIG. 1 is a block diagram showing an overview of a sensing system according to an exemplary embodiment of the present invention.
Figure 2:
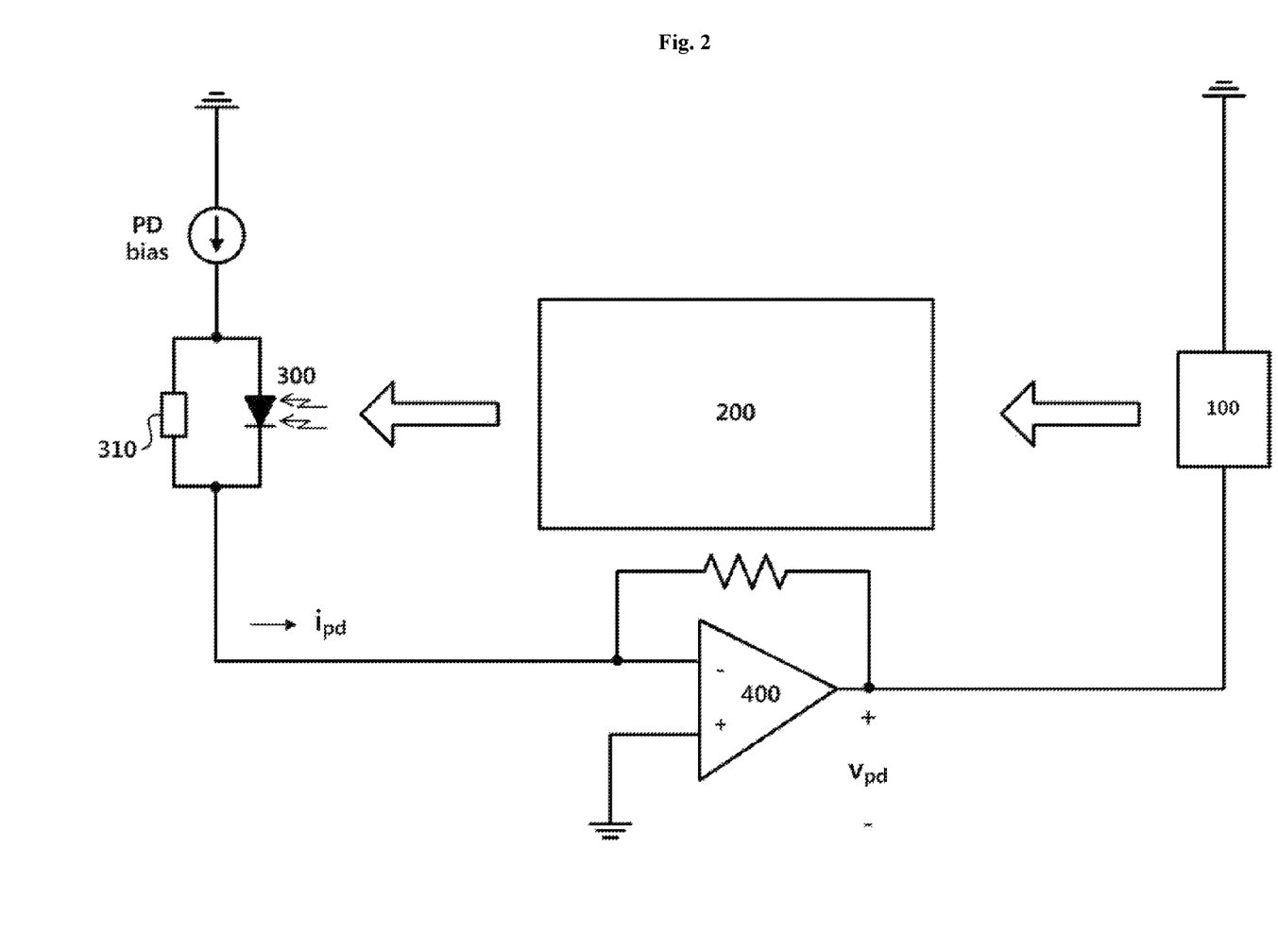
FIG. 2 is a schematic circuit diagram of the sensing system according to the exemplary embodiment of the present invention.

Hereinafter, exemplary embodiments of the present invention will be described with reference to the accompanying drawings. FIG. 1 is a block diagram showing an overview of a sensing system according to an exemplary embodiment of the present invention, and FIG. 2 is a schematic circuit diagram of the sensing system according to the exemplary embodiment of the present invention. Referring to FIGS. 1 and 2, the sensing system according to the present embodiment includes an actuator 100. In the present embodiment, actuators may be roughly classified into two main types according to stimuli provided by the actuators. A first type may be an optical actuator which receives a bias and applies an optical stimulus. An optical actuator may provide, for example, ultraviolet light, visible light, infrared light, and laser light. A second type is a non-optical actuator which receives a bias and provides a non-optical stimulus to a medium 200. A non-optical actuator applies non-optical stimuli, for example, a sonic wave, a supersonic wave, a magnetic field, an electric field, radioactivity, and so on.

Figure 3A:
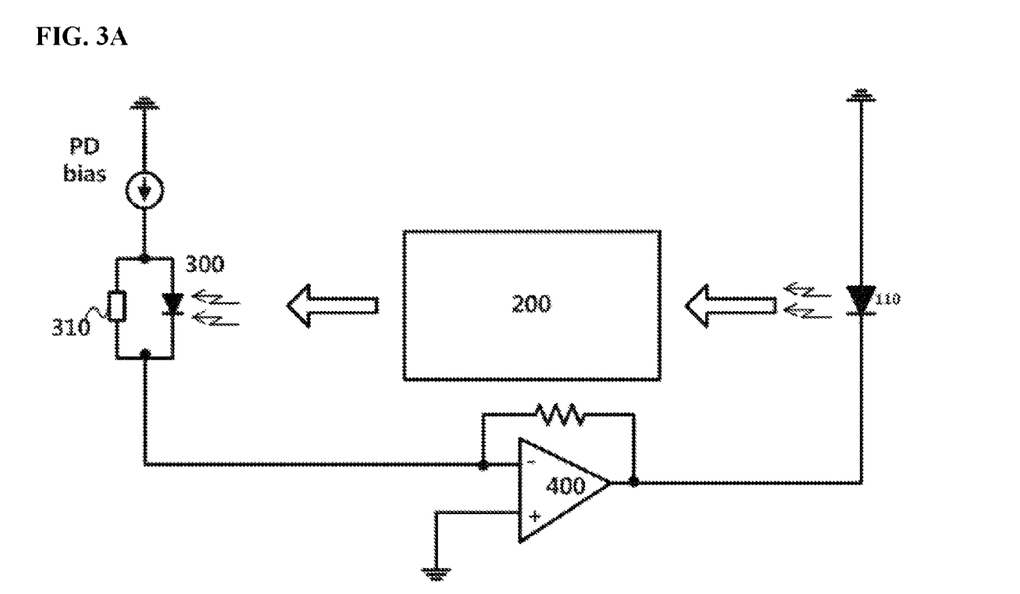
FIG. 3A is a diagram showing an example in which a light-emitting diode (LED) is used as an optical actuator.

An optical actuator may be implemented as, for example, a light-emitting diode (LED), a laser diode (LD), etc. which receives a bias and provides light. FIG. 3A shows an example in which an LED 110 is used as an optical actuator. An LED may emit light of a visible light, ultraviolet light, or infrared light wavelength band, and an LD may emit laser light having a specific band in a band from 270 nm to 3330 nm. It is preferable to provide an optical actuator which emits light having a band appropriate for characteristics of a material to be detected by the sensing system.

Figure 3B:
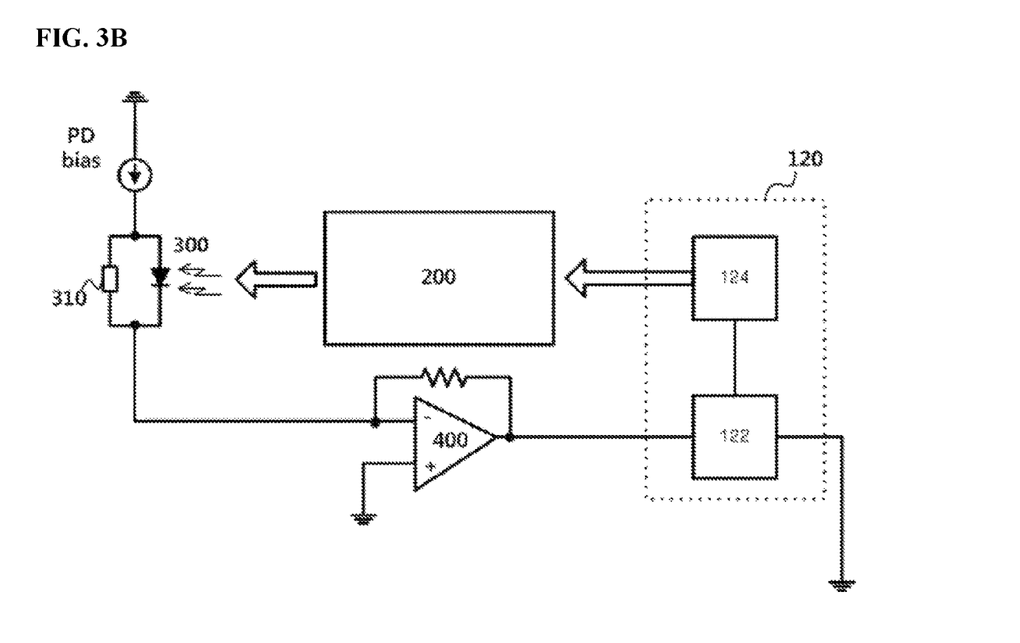
FIG. 3B is a diagram showing an example in which a non-optical actuator is implemented with a supersonic actuator.

A non-optical actuator may be implemented as a supersonic actuator which receives a bias and provides a supersonic wave, a magnetic actuator which provides a magnetic field, an electric actuator which provides an electric field, a radioactive actuator which provides radioactivity, and so on. FIG. 3B shows an example in which a non-optical actuator is implemented with a supersonic actuator 120. The supersonic actuator 120 includes a driver 122 and a piezoelectric transducer 124. The driver 122 provides an alternating current (AC) signal having an amplitude corresponding to a voltage difference between both ends thereof to the piezoelectric transducer 124, and the piezoelectric transducer 124 provides a supersonic wave having an intensity corresponding to the amplitude of the received AC signal to the medium 200.

An optical actuator provides an optical stimulus, and a non-optical actuator provides a non-optical stimulus. In other words, each actuator performs a common function of receiving a bias and providing a stimulus to a degree corresponding to the bias. For convenience of description, an exemplary embodiment in which an optical stimulus is provided by an optical actuator will be mainly described below. However, this is merely for convenience of description and should not be interpreted as limiting the scope of the present invention.

Referring back to FIGS. 1 and 2, the medium 200 includes a detection-target material which is to be detected by the sensing system according to the present embodiment. The detection-target material receives a stimulus from the actuator 100 and produces an optical reaction. For example, bovine serum albumin (BSA) has a characteristic of absorbing light having a 270 nm to 280 nm wavelength. Therefore, when laser light having a 275 nm wavelength is emitted to a medium including BSA, the BSA produces an optical reaction of absorbing the incident light in response to the provided optical stimulus. However, this is merely an example for description, and a detection-target material, an optical stimulus provided to the detection-target material, and an optical reaction to the optical stimulus brought about according to the detection-target material may vary.

A photo-detector 300 detects an optical reaction which is produced by a stimulus provided to the medium 200, and outputs the detected optical reaction as an electrical signal. The optical reaction may vary according to a concentration of the detection-target material included in the medium 200, and the electrical signal provided by the photo-detector 300 may also vary accordingly. In an exemplary embodiment, the photo-detector 300 may be implemented with a photodiode, and the photodiode may detect a change in light caused by an optical reaction brought about in the medium 200 and provide a current corresponding to the changed light.

In an exemplary embodiment, the photo-detector 300 may be provided with a drive current $i_{pd}$ from a power source PD bias which provides a bias current, and the sensing system according to the present embodiment detects an optical reaction produced by the medium 200 while sweeping the drive current $i_{pd}$ provided by the power source PD bias. As will be described below, when the drive current $i_{pd}$ sweeps, the photo-detector 300 outputs an electrical signal having a snapback form.

An amplifier 400 amplifies the electrical signal provided by the photo-detector 300 and outputs the amplified electrical signal, and the amplified electrical signal is summed with the bias of the actuator 100 and fed back to the actuator 100. Therefore, the actuator 100, the medium 200, the photo-detector 300, and the amplifier 400 form a positive feedback path. In an exemplary embodiment, the amplifier 400 may be implemented as a current-voltage (I-V) converter which converts the current provided by the photodiode into the form of a voltage signal, and an output voltage of the I-V converter is positively fed back together with a bias ACT bias of the optical actuator 100.

The current $i_{pd}$ provided by the photo-detector 300 is converted into a voltage signal $v_{pd}$ by the amplifier 400. Since the voltage signal $v_{pd}$ has a negative potential, a potential of one end of the optical actuator 100 connected to the amplifier 400 becomes lower than a potential of the other end connected to a reference potential. When the voltage $v_{pd}$ of the amplifier 400 increases, the bias applied to the optical actuator 100 increases and a stronger optical stimulus is provided. Accordingly, the medium 200 optically reacts to the provided optical stimulus, and the photo-detector 300 which detects the optical reaction provides the larger current $i_{pd}$. In other words, it is possible to see that the sensing system according to the present embodiment has the positive feedback path.

In an exemplary embodiment, the photo-detector 300 may be implemented as a photodiode. Since a current output from the photodiode is converted into a voltage signal and amplified by the amplifier 400 and operates the optical actuator 100, the current provided by the photodiode is required to be sufficiently high so that the amplifier 400 outputs a voltage suitable to turn on the optical actuator 100.

Due to a characteristic of the photodiode biased in reverse and operated, the photodiode is required to operate near a breakdown voltage so that a sufficiently high current may be obtained from the photodiode. However, a breakdown may be caused by the reverse bias, and a problem may occur in the reliability of operation of the photodiode.

To provide a sufficiently high current to the amplifier 400 when the reverse voltage provided to the photodiode is low, a voltage clamping device 310 which clamps the voltage applied to the photodiode by preventing the voltage from increasing to a target voltage or higher is connected in parallel with the photodiode. The voltage clamping device 310 prevents the voltage provided to both ends thereof from increasing to a predetermined clamping voltage value or more. Therefore, by connecting the voltage clamping device 310 having the predetermined clamping voltage in parallel with the photodiode, it is possible to prevent an application of a reverse voltage which is so high that the reliability of the photodiode may be degraded.

Figure 4A:
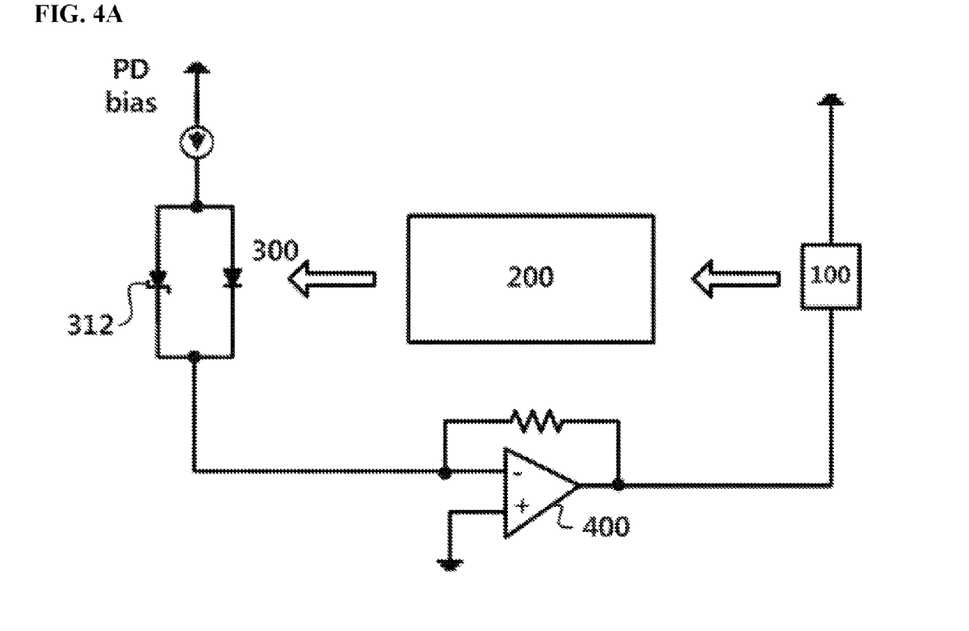
FIG. 4A is a diagram showing an example in which a voltage clamping device is implemented with a Zener diode.

In an exemplary embodiment, as shown in FIG. 4A, a voltage clamping device may be implemented as a Zener diode 312 which uses a Zener breakdown phenomenon. When a voltage of a Zener breakdown voltage Vz (see FIG. 4B) or higher is applied in reverse to the Zener diode 312, the Zener breakdown phenomenon occurs. Then, a reverse current is not blocked but flows, and the voltage is clamped so that an application of the voltage of the Zener breakdown voltage Vz or higher to both ends of the Zener diode may be prevented.

Figure 4B:
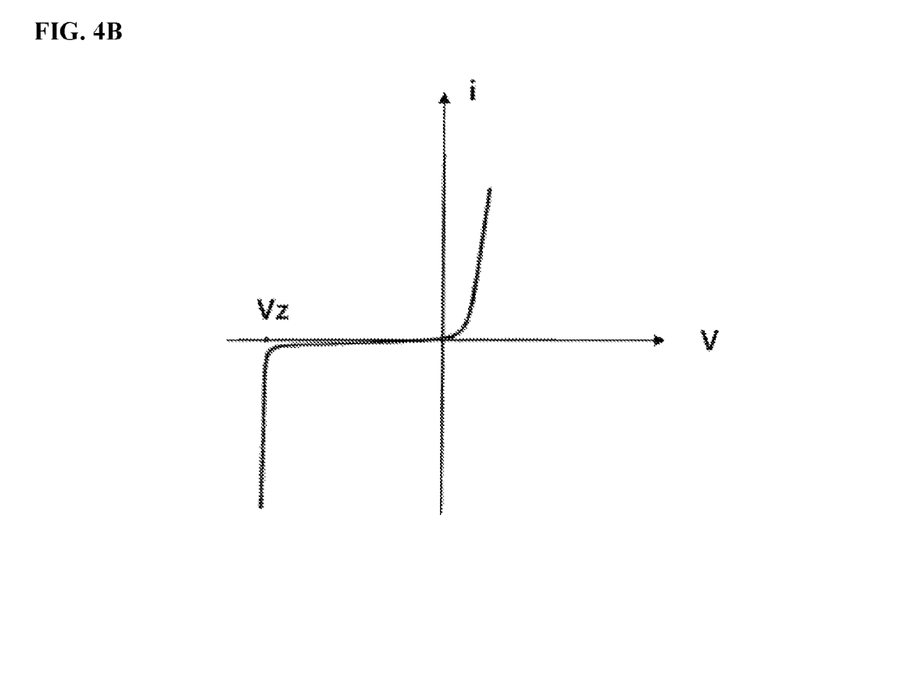
FIG. 4B is the voltage-current characteristic curve of a Zener diode.

Also, referring to FIG. 4B, when a voltage at which the photodiode operates is set to cause a Zener breakdown, it is possible to flow a current sufficient to be converted by the amplifier 400 into a voltage for operating the actuator 100. Therefore, when the photodiode and the Zener diode 312 are connected in parallel, it is possible to provide a sufficient current without applying a voltage equal to or higher than a voltage degrading the reliability of the photodiode.

Referring back to FIGS. 1 and 2, a detector 500 is provided with an electrical signal output by the photo-detector 300 and analyzes the electrical signal to detect a concentration of the detection-target material included in the medium 200. In an exemplary embodiment, the detector 500 has a read-out circuit to analyze an electrical signal OUTPUT provided by the photo-detector 300 and detect the concentration of the detection-target material.

Figure 5:
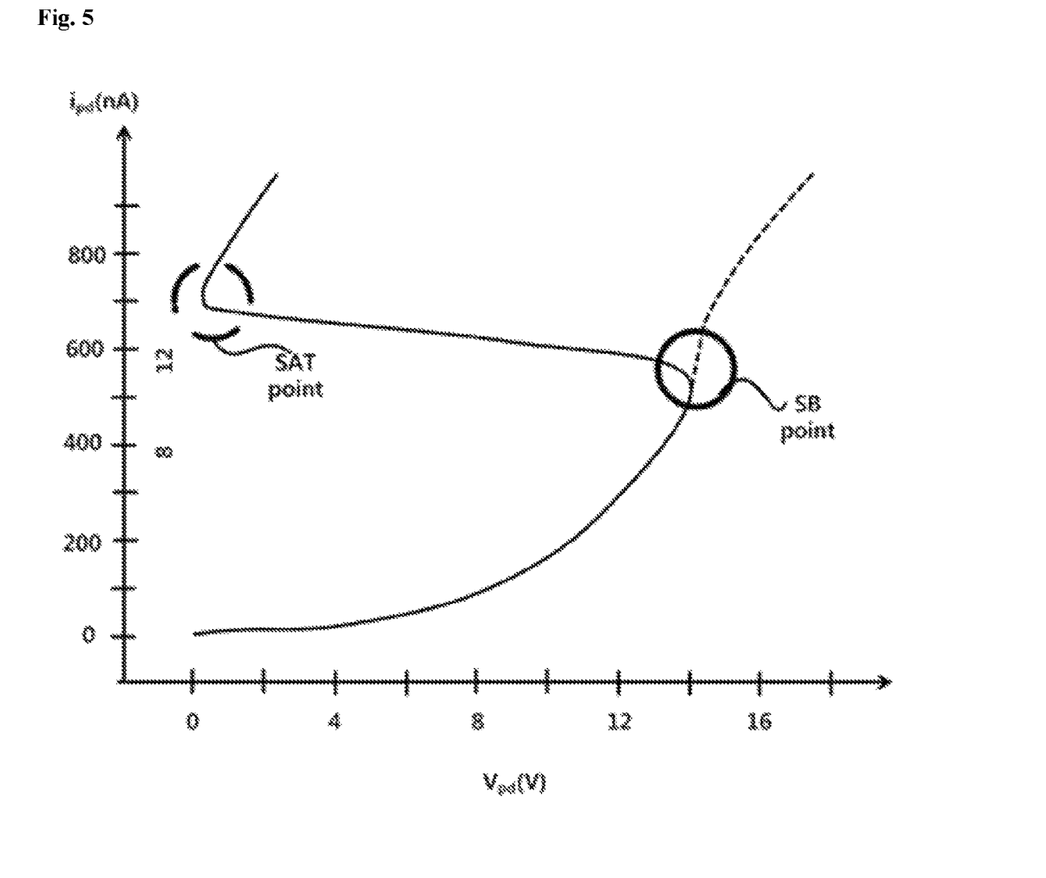
FIG. 5 is a voltage-current characteristic curve showing an overview of an electrical signal output by a photo-detector when the sensing system according to the exemplary embodiment detects bovine serum albumin (BSA) which is a detection-target material.

FIG. 5 is a voltage-current characteristic curve showing an overview of an electrical signal output by the photo-detector 300 when the sensing system according to the exemplary embodiment detects BSA which is a detection-target material. The vertical axis denotes values of the bias current $i_{pd}$ applied to the photo-detector 300 of FIGS. 1 and 2, and the horizontal axis denotes values of the voltage $v_{pd}$ appearing at both ends of the photo-detector 300.

A change of the voltage at both ends of the photo-detector 300 while the bias current provided to the photo-detector 300 is increased from 0 will be described with reference to FIGS. 1, 2, and 5. When the bias current $i_{pd}$ provided to the photo-detector 300 increases, the voltage $v_{pd}$ appearing at both ends of the photo-detector 300 increases accordingly, but the optical actuator 100 is not yet turned on.

With the increase in the current applied to the photo-detector 300, the amplifier 400 applies a voltage equal to or higher than a turn-on voltage to the optical actuator 100, thereby turning on the optical actuator 100. The turned-on optical actuator 100 provides an optical stimulus to the medium 200, and when the medium 200 emits light as an optical reaction, the photo-detector 300 detects the light, converts the light into a current, and outputs the current. At a time point at which the photo-detector 300 is turned on, in order for the photo-detector 300 to flow a constant current, it is necessary to compensate for a current generated by the light emitted by the medium 200 as the optical reaction, and thus the voltage at both ends of the photo-detector 300 should be reduced. Therefore, the voltage is reduced. In other words, a negative resistance characteristic, that is, the voltage applied to both ends of the photo-detector 300 decreases even when the power source PD bias increases the current applied to the photo-detector 300, is exhibited. Such a phenomenon that a both-end voltage of the photo-detector 300 decreases with the increase in the current applied to the photo-detector 300 is called a snapback phenomenon. Also, a starting point of the snapback phenomenon is called an SB point, and a section in which the voltage decreases in spite of an increase in the current due to the snapback phenomenon is called an SB section.

When the bias current of the photo-detector 300 is further increased, the voltage at both ends of the photo-detector 300 is reduced be close to about 0. This is called a saturation (SAT) point, and a section behind the SAT point is called an SAT section. With the increase in the bias current of the photo-detector 300, the medium 200 consequently provided with a stronger optical stimulus due to a positive feedback provides light to the photo-detector 300 as a stronger optical reaction. The photo-detector 300 should reduce the both-end voltage so as to compensate for a current generated by the stronger light, and it is determined that SAT occurs for this reason. With a continuous increase in the bias current, the voltage at both ends of the photo-detector 300 is kept around this point. In other words, there is almost no change in the voltage with an increase in the current. FIG. 5 shows that the voltage may increase by about several volts, but referring to FIG. 6 showing a current-voltage characteristic when a voltage of about 100 V is applied to both ends of the photo-detector 300, it is possible to see that a change in the voltage with respect to a change in the current is slight in the SAT section.

A dotted curve in FIG. 5 is a current-voltage characteristic curve obtained when a signal path is an open loop without a positive feedback path. Since the optical actuator 100, the medium 200, the photo-detector 300, and the amplifier 400 are connected for a positive feedback, it is possible to see the snapback characteristic compared to the dotted curve.

Figure 6:
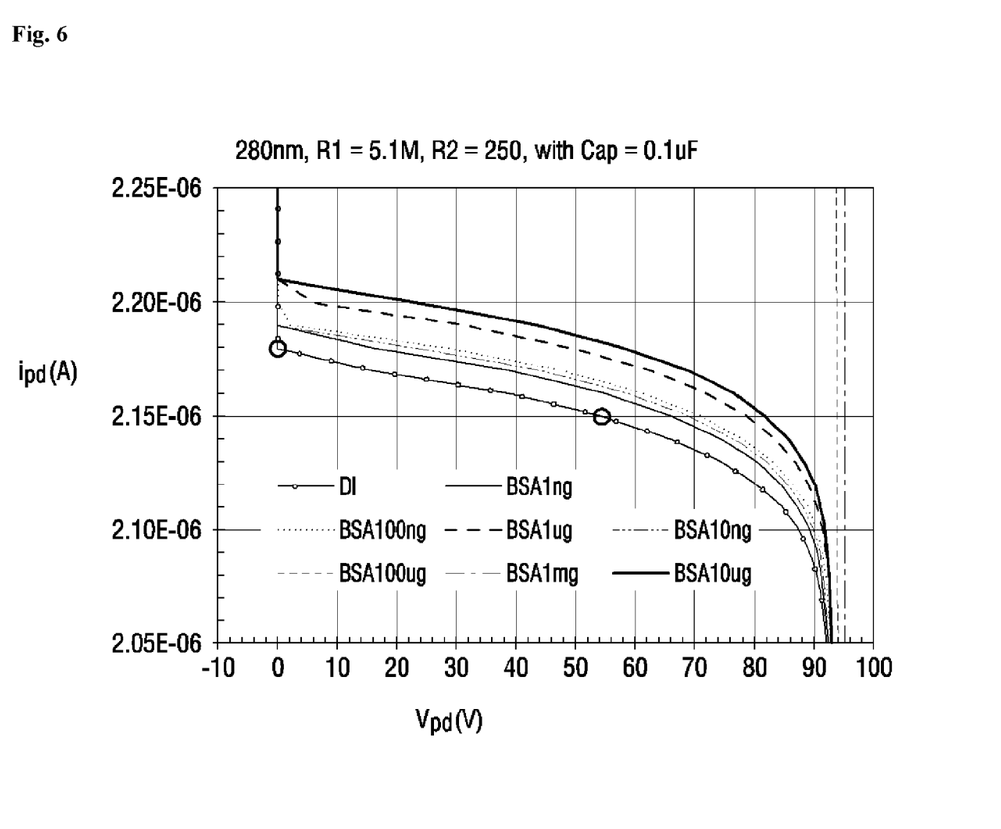
FIG. 6 is a graph showing results of measuring current-voltage characteristics according to concentrations of a detection-target material in a snapback (SB) section.

FIG. 6 is a graph showing results of measuring current-voltage characteristics according to concentrations of a detection-target material in an SB section. Current-voltage curves of FIG. 6 are obtained when the sensing system according to the present embodiment detects BSA that is the detection-target material in mediums obtained by adding 1 ng, 10 ng, . . . , and 1 mg BSA to deionized water (DI). As shown in the drawing, an SB occurs when a current of about 2.1 μA to about 2.15 μA is applied to the photo-detector 300, and SAT occurs at a current of 2.17 μA to 2.21 μA and a voltage of about 0 V.

It is possible to see that the current-voltage characteristics vary in the SB section according to concentrations of the detection-target material. Therefore, the detector 500 may determine the concentration of the detection-target material by fixing the bias current of the photo-detector 300 and reading the both-end voltage of the photo-detector 300 or by fixing the both-end voltage of the photo-detector 300 and then reading the bias current of the photo-detector 300. For example, when the both-end voltage of the photo-detector 300 is read as 66 V after the bias current of the photo-detector 300 is fixed at 2.15 μA, the detector 500 may determine that the concentration of the detection-target material is 1 ng. In another example, when the bias current of the photo-detector 300 is read as 2.18 μA after the both-end voltage of the photo-detector 300 is fixed at 40 V, the detector 500 may determine that the concentration of the detection-target material is 100 ng. In addition, by measuring current and voltage values at the SAT point behind the SB section, it is possible to measure the concentration of the detection-target material. Further, by selecting two points between the SB point and the SAT point and detecting a change in the both-end voltage while sweeping the current, it is possible to calculate a resistance value and measure the concentration of the detection-target material.

For example, in the case of the medium obtained by adding 100 μg BSA to DI shown in FIG. 5, the current rises from 2.15 μA to 2.18 μA, that is, by 0.03 while the both-end voltage of the photo-detector 300 decreases from about 55 V to about 0 V. An average resistance value in the corresponding section is calculated to be about 1.833 GΩ. In the current-voltage curves shown in FIG. 6, the photo-detector 300 has a resistance value of giga-ohms or higher.

Figure 7A:
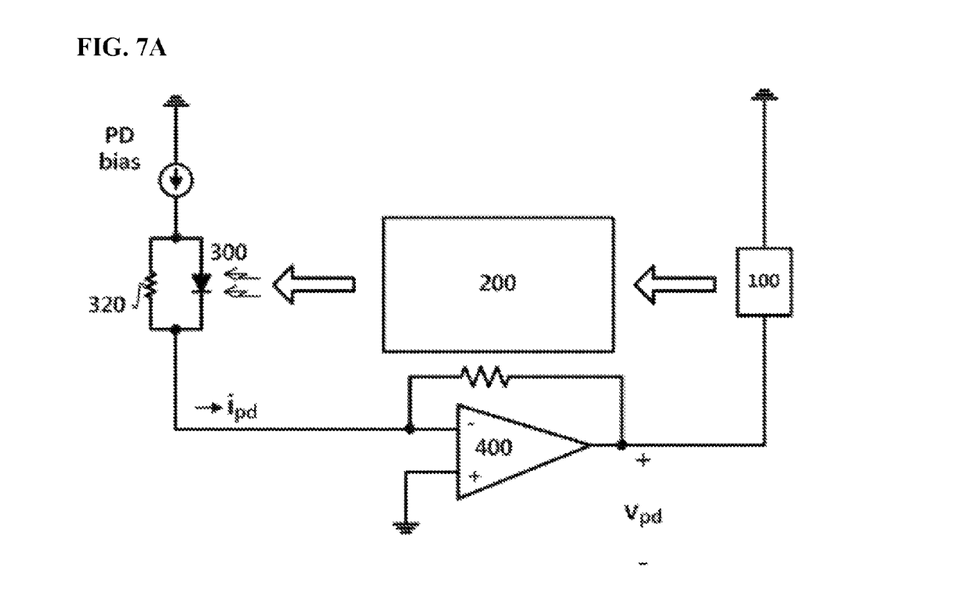
FIG. 7A is a diagram showing an example in which a resistance is connected in parallel with a photo-detector.

FIG. 7A is a diagram showing an example in which a resistance 320 is connected in parallel with a photo-detector. When resistances $R_1$ and $R_2$ are connected in parallel, an equivalent resistance value $R_{eq}$ is calculated by Equation 1 below.

$$R_{eq} = \frac{R_1 \times R_2}{R_1 + R_2} \quad \text{[Equation 1]}$$

When the resistances $R_1$ and $R_2$ have the relationship $R_1 \gg R_2$, the equivalent resistance value $R_{eq}$ may be approximated by Equation 2 below.

$$R_{eq} = \frac{R_1 \times R_2}{R_1 + R_2} = \frac{R_2}{1 + \frac{R_2}{R_1}} = R_2 (R_1 \gg R_2) \quad \text{[Equation 2]}$$

When two resistances any one of which has a larger resistance value than the other are connected in parallel, an equivalent resistance value for the resistances connected in parallel is approximated to a smaller resistance value. Therefore, when a photo-detector having a large resistance and a photo-detector having a smaller resistance are connected in parallel, an equivalent resistance value for the two photo-detectors connected in parallel may be approximated to the smaller resistance value, and the equivalent resistance may be formed to be easily measured without using expensive measuring equipment.

For example, a resistance value of a resistance 320 connected in parallel with the photo-detector 300 may be adjusted according to a material to be detected by the sensing system according to the present embodiment and a concentration of the material. In another example, the resistance value of the resistance 320 connected in parallel with the photo-detector 300 may be adjusted so that an equivalent resistance value for the photo-detector 300 and the resistance 320 is included in a measurement range of measuring equipment for measuring the equivalent resistance value.

Figures 7B, 7C:
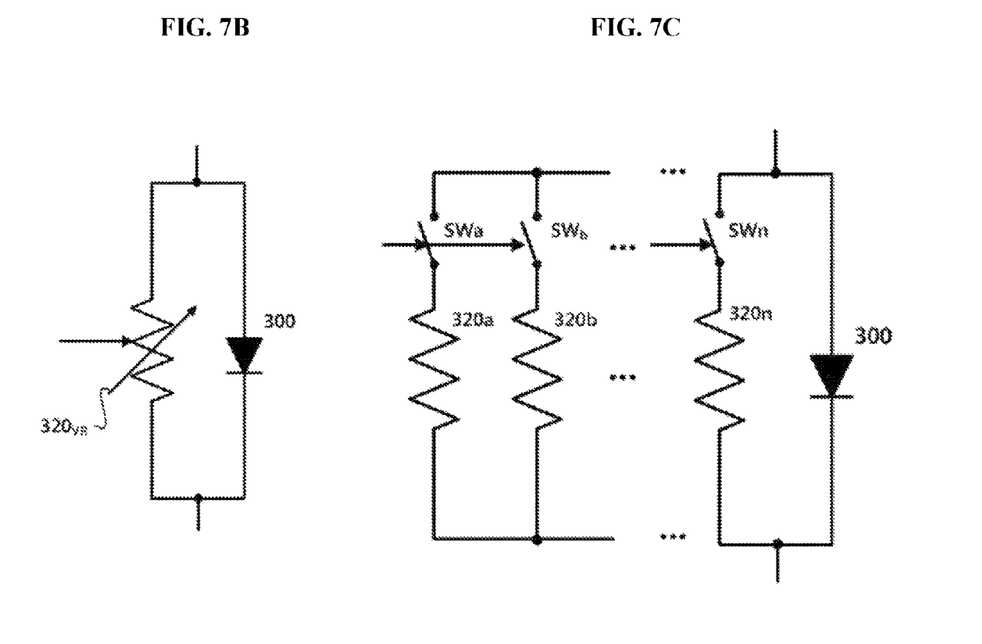
FIGS. 7B and 7C are diagrams showing implementation examples of a resistance which is connected in parallel with the photo-detector.

In an exemplary embodiment, the resistance value of the resistance 320 connected in parallel with the photo-detector 300 may be controlled and changed. For example, as shown in FIG. 7B, the resistance 320 connected in parallel with the photo-detector 300 may be a variable resistance $320_{VR}$ which is controlled electrically or manually. In another example, as shown in FIG. 7C, the resistance 320 connected in parallel with the photo-detector 300 may include a plurality of resistances 320a, 320b, . . . , and 320n and switches SWa, SWb, . . . , and SWn for controlling connections among the plurality of resistances 320a, 320b, . . . , and 320n, and may have a target resistance value through conduction control by the switches SWa, SWb, . . . , and SWn. According to Equation 1, when $R_1$ and $R_2$ have the same resistance value, the equivalent resistance value $R_{eq}$ is $R_1/2$. Further, when n resistances having the same resistance value of R are connected in parallel, the equivalent resistance value $R_{eq}$ is R/n. Therefore, by controlling connections among the plurality of resistances 320a, 320b, . . . , and 320n whose resistance values are known with the switches SWa, SWb, . . . , and SWn, it is possible to determine an equivalent resistance value of the resistances 320a, 320b, . . . , and 320n connected in parallel with the photo-detector 300.

Implementation Examples and Experimental Results

Figure 8:
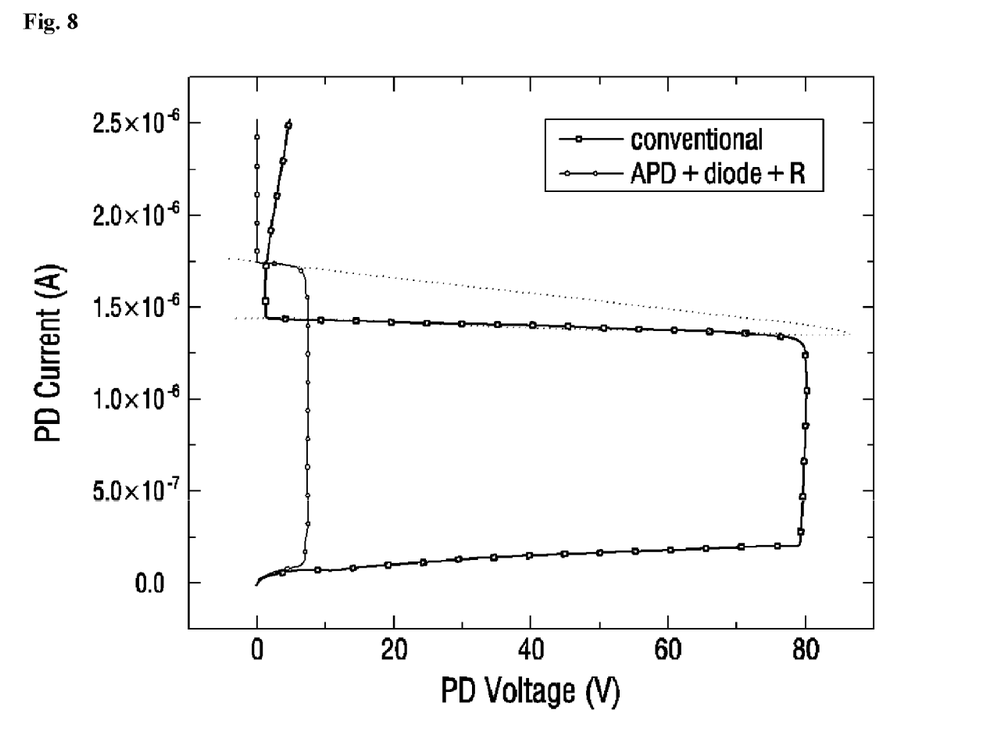
FIG. 8 is a graph showing results of measuring a voltage-current characteristic when a photodiode, a resistance, and a voltage clamping device are connected in parallel using a 300 MΩ resistance and a Zener diode with a Zener breakdown voltage of 7 V as the voltage clamping device.

Experimental results of detecting a detection-target material with the sensing system according to the exemplary embodiment of the present invention will be described below. FIG. 8 is a graph showing results of measuring a voltage-current characteristic when a photodiode, a resistance, and a voltage clamping device are connected in parallel using a 300 MΩ resistance and a Zener diode with a Zener breakdown voltage of 7 V as the voltage clamping device.

In a sensing system according to a prior art represented by a black line, when a current of about 1.48 µA was provided to a photodiode, a voltage of 80 V appeared at both ends of the photodiode, and an SB occurred. On the other hand, in the present embodiment represented by a red line, when a current of about 1.70 µA was provided, a voltage of 7 V, which is a Zener breakdown voltage, appeared at both ends of the photodiode, and an SB occurred.

Therefore, unlike the related art, the present embodiment does not require a voltage which is close to or exceeds the breakdown voltage of the photodiode, and makes it possible to obtain a higher current by providing a lower voltage compared to the related art.

In the sensing system according to a prior art, an SB point was at 1.33 µA and 80 V, and an SAT point was at 1.47 µA and 1.42 V. In an SB section from the SB point to the SAT point, an average resistance value was calculated to be −561 MΩ. In the present embodiment, an SB point was at 1.72 µA and 7 V, and an SAT point was at 1.76 µA and 0 V. In an SB section from the SB point to the SAT point, an average resistance value was calculated to be −175 MΩ. Consequently, it is possible to see that the equivalent resistance value is reduced to about one-third of the equivalent resistance value of the related art.

According to the sensing system of the present embodiment, it is possible to detect a detection-target material whose concentration is too low to be detected by an existing sensor, and to obtain reliable operation of a photo-detector because it is unnecessary to apply an excessive reverse voltage to be provided with a sufficient current from the photo-detector. Further, measuring is possible without using expensive equipment.

It should be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A sensing system comprising:
    an actuator configured to provide a stimulus to a detection-target material;
    a photo-detector configured to output an electrical signal corresponding to an optical reaction brought about according to a concentration of the detection-target material provided with the stimulus;
    an amplifier configured to amplify the electrical signal output from the photo-detector and apply the amplified electrical signal to the actuator in a positive feedback manner;
    a detector configured to receive the electrical signal and detect the detection-target material; and
    a voltage clamping device connected in parallel with the photo-detector and configured to clamp a voltage at both ends of the photo-detector so that the voltage does not exceed a predetermined voltage value,
    wherein the electrical signal has a snapback form due to the positive feedback.

2. The sensing system of claim 1, further comprising a power source configured to apply a bias current to the photo-detector.

3. The sensing system of claim 1, wherein the photo-detector includes a photodiode.

4. The sensing system of claim 1, wherein the voltage clamping device is a Zener diode, and
    the predetermined value is a Zener breakdown voltage value of the Zener diode.

5. The sensing system of claim 1, further comprising a resistance connected in parallel with the photo-detector.

6. A sensing system comprising:
    an actuator configured to provide a stimulus to a detection-target material;
    a photo-detector configured to output an electrical signal corresponding to an optical reaction brought about according to a concentration of the detection-target material provided with the stimulus;
    an amplifier configured to amplify the electrical signal output from the photo-detector and apply the amplified electrical signal to the actuator in a positive feedback manner;
    a detector configured to receive the electrical signal and detect the detection-target material; and
    a resistance connected in parallel with the photo-detector,
    wherein a resistance value of the resistance is determined so that an equivalent resistance for the photo-detector and the resistance connected in parallel has a smaller resistance value than a equivalent resistance for the photo-detector,
    wherein the electrical signal has a snapback (SB) due to the positive feedback.

7. The sensing system of claim 6, further comprising a power source configured to apply a bias current to the photo-detector.

8. The sensing system of claim 6, wherein the resistance is any one of a fixed resistance having a fixed resistance value and a variable resistance.

9. The sensing system of claim 8, wherein the resistance value of the variable resistance is controlled electrically or manually.

10. The sensing system of claim 6, wherein the resistance includes a plurality of resistances each having one end connected to a first common node and the other end connected to a second common node through each switch,
    the first common node and the second common node are connected to one end and the other end of the photo-detector respectively, and
    opening and closing of the switches is controlled to adjust the resistance value of the equivalent resistance for the photo-detector and the resistance connected in parallel.

11. The sensing system of claim 6, further comprising a voltage clamping device connected in parallel with the photo-detector.

* * * * *